(12) United States Patent
Latham et al.

(10) Patent No.: US 8,956,566 B2
(45) Date of Patent: Feb. 17, 2015

(54) SYSTEM AND METHOD FOR VIRUS INACTIVATION

(71) Applicants: Peter W. Latham, Acton, MA (US); Nigel Grinter, Buffalo Grove, IL (US); Robert Sever, Arlington Heights, IL (US)

(72) Inventors: Peter W. Latham, Acton, MA (US); Nigel Grinter, Buffalo Grove, IL (US); Robert Sever, Arlington Heights, IL (US)

(73) Assignee: Pure Biosolutions, LLC, Maynard, MA (US)

(*) Notice: Subject to any disclaimer, the term of this patent is extended or adjusted under 35 U.S.C. 154(b) by 0 days.

(21) Appl. No.: 13/796,848

(22) Filed: Mar. 12, 2013

(65) Prior Publication Data

US 2013/0236358 A1    Sep. 12, 2013

Related U.S. Application Data

(60) Provisional application No. 61/609,409, filed on Mar. 12, 2012, provisional application No. 61/639,459, filed on Apr. 27, 2012.

(51) Int. Cl.
*A61L 9/00* (2006.01)
*A61L 2/00* (2006.01)
*B08B 7/00* (2006.01)
*B08B 9/00* (2006.01)
*A61L 2/18* (2006.01)

(52) U.S. Cl.
CPC *A61L 2/0094* (2013.01); *A61L 2/18* (2013.01)
USPC .......... 422/28; 422/1; 422/32; 422/33; 134/6; 134/21; 134/22.6; 134/22.17; 134/22.18

(58) Field of Classification Search
CPC .......... A61L 2/00; A01N 1/00; A01N 1/0215; C12H 1/00
USPC .......... 422/1, 28, 32–33, 295; 134/6, 21, 22.6, 134/22.17, 22.18, 26, 61; 435/1.1, 1.2
See application file for complete search history.

(56) References Cited

U.S. PATENT DOCUMENTS

| | | |
|---|---|---|
| 4,511,556 A | 4/1985 | Purcell et al. |
| 4,613,501 A | 9/1986 | Horowitz |
| 5,055,485 A | 10/1991 | Geacintov et al. |
| 5,877,005 A | 3/1999 | Castor et al. |
| 6,465,168 B1 | 10/2002 | Castor et al. |

(Continued)

*Primary Examiner* — Monzer R Chorbaji
(74) *Attorney, Agent, or Firm* — McCarter & English, LLP

(57) ABSTRACT

Methods and systems for virus inactivation in the production or processing of biological or other sensitive substances are provided. The disclosed methods and systems for virus inactivation involve the key steps of dissolving carbon dioxide into biological or other sensitive substances; and treating the substance with the dissolved carbon dioxide at conditions which are less than critical pressure and temperature for a prescribed treatment time to inactivate at least 80% of the target virus or viruses contained within the biological or other sensitive substances. The disclosed carbon dioxide treatments for virus inactivation may optionally include concurrently or sequentially subjecting the substances with an acid treatment to lower the pH of the substance and inactivate viruses contained within the biological or other sensitive substance. Operating conditions for the disclosed carbon dioxide treatments preferably involve sparging carbon dioxide gas into the substance until the composition is saturated with carbon dioxide and is conducted at pressures below about 5 MPa; at temperatures of less than or equal to 30° C.; and for a treatment time of between about one minute and about 2000 minutes.

17 Claims, 3 Drawing Sheets

(56) References Cited

U.S. PATENT DOCUMENTS

| | | |
|---|---|---|
| 6,613,278 B1 * | 9/2003 | Mills et al. .................. 422/33 |
| 7,008,591 B2 | 3/2006 | Kafesjian et al. |
| 7,033,813 B2 | 4/2006 | Castor et al. |
| 2005/0084532 A1 | 4/2005 | Howdle et al. |
| 2006/0269928 A1 | 11/2006 | Castor |
| 2007/0190158 A1 | 8/2007 | Hwang et al. |
| 2009/0087471 A1 | 4/2009 | Shimp et al. |
| 2010/0329971 A1 | 12/2010 | Yamamoto et al. |
| 2011/0059040 A1 | 3/2011 | Kiser et al. |

* cited by examiner

Fig. 5

| Table 1 | MS2 Phage Plaques Counted | | | T7 Phage Plaques Counted | | |
|---|---|---|---|---|---|---|
| Dilution of phage | Liquid $N_2$ | Frozen with dry ice ($CO_2$) | Untreated | Liquid $N_2$ | Frozen with dry ice ($CO_2$) | Untreated |
| $10^{-2}$ | TNTC | TNTC | TNTC | TNTC | TNTC | TNTC |
| $10^{-3}$ | TNTC | TNTC | TNTC | TNTC | TNTC | TNTC |
| $10^{-4}$ | TNTC | TNTC | TNTC | TNTC | TNTC | TNTC |
| $10^{-5}$ | TNTC | TNTC | TNTC | TNTC | TNTC | TNTC |
| $10^{-6}$ | 37, 26 | 15, 13 | 23, 17 | 3, 2 | 0, 0 | 3, 1 |

Fig. 6

| Table 2 | MS2 Phage Plaques Counted | | | T7 Phage Plaques Counted | | |
|---|---|---|---|---|---|---|
| Dilution of phage | Liquid $N_2$ | 90 psi $CO_2$ | Untreated | Liquid $N_2$ | 90 psi $CO_2$ | Untreated |
| $10^{-2}$ | TNTC | TNTC | TNTC | TNTC | TNTC | TNTC |
| $10^{-3}$ | TNTC | TNTC | TNTC | TNTC | TNTC | TNTC |
| $10^{-4}$ | TNTC | TNTC | TNTC | TNTC | TNTC | TNTC |
| $10^{-5}$ | TNTC | 19, 21 | TNTC | 6, 7 | 3, 9 | 3, 4 |
| $10^{-6}$ | 22, 29 | 0, 0 | 20, 25 | 0 | 0 | 0 |

SYSTEM AND METHOD FOR VIRUS INACTIVATION

CROSS REFERENCE TO RELATED APPLICATIONS

This application claims priority to U.S. Provisional Application Ser. No. U.S. 61/609,409, filed Mar. 12, 2012, and U.S. Provisional Application Ser. No. 61/639,459, filed Apr. 27, 2012, the entirety of each are incorporated herein by reference.

FIELD OF THE INVENTION

The present disclosure relates to systems and methods for virus inactivation in biological and other sensitive substances and related materials and, more particularly, the use of carbon dioxide at conditions below its critical or supercritical state, alone, or in conjunction with other virus inactivation techniques, for example, low pH or acid treatments.

BACKGROUND

Viruses, which are known to cause human disease (e.g., colds, influenza, polio, AIDS, etc.), are not considered live cells in the traditional sense but infect living cells where they can replicate. Viruses may exist in the living cells used to produce biopharmaceutical products, thereby presenting a serious risk of contaminating the biopharmaceutical products during processing. In addition, viruses can be introduced into biopharmaceutical products through reagents fed to the process (especially of concern is cell culture media including components derived from animal origin) and through accidental exposure to the processing environment or personnel. Such contaminating viruses must be removed or inactivated prior to (e.g., in the case of inactivating viruses in the cell culture media prior to introduction in the facility or process), during, or after the manufacturing or processing of the product without harming or destroying the often delicate biopharmaceutical or other sensitive product.

In addition to biopharmaceutical and biologically derived products, there are many other sensitive products including synthetic media, blood, cell therapy, protein, small molecule pharmaceuticals, nutrition products, infant formula, liquid or non-liquid form of all, that must be manufactured and delivered free of active viruses.

For many biopharmaceutical products, the United States Food and Drug Administration (FDA) requires less than one virus per million doses of product sold. To achieve this target, current virus control strategies used in biopharmaceutical manufacturing operations often utilize multiple inactivation techniques. One of the most common techniques is virus filtration, generally using direct flow filtration. Another common method is low pH inactivation, in which the solution containing the biopharmaceutical product is held in a vessel and treated with acid. The efficacy of inactivation depends not only on the sensitivity of the virus to the acidic conditions, but also on the sensitivity of the biopharmaceutical product. The pH level and time of exposure to the acidic conditions are chosen so as to minimize any damage to the resulting biopharmaceutical product.

Chromatography is the most common technique for purifying the desired biopharmaceutical product from other synthesis by-products or wastes, and biopharmaceutical manufacturers leverage their chromatography steps to further augment their virus safety assurance. For example, it has been shown that a number of protein denaturants commonly used in gel affinity chromatography for protein elution and gel recycling (e.g., sodium thiocyanate or urea), can significantly inactivate viruses.

Other chemical treatments have also been shown to be effective for virus inactivation. For example, solvent/detergent (S/D) treatment is commonly used to inactivate enveloped viruses by disrupting the lipid envelope surrounding the viruses. Chemical treatments may necessitate additional purification and filtration processing to remove the chemicals from the product solution after virus inactivation is complete.

High temperature pasteurization can also be effective for inactivating viruses, although additional stabilizers are often required in the product solution to help the biopharmaceutical product withstand pasteurization conditions. In the case of high temperature, short time viral inactivation sometimes used on cell culture media, specific components are degraded by the process and must be removed, then added back to the media after processing, reducing the potential efficacy of the viral inactivation.

Other contemplated means for virus inactivation involve the use of carbon dioxide at very high pressures, including at or near supercritical conditions. See, for example, U.S. Pat. No. 5,877,005 (Castor et al.).

There has been extensive work to quantify the effects of carbon dioxide on biological materials, and in particular microbes, spores, and proteins. While the effects of using carbon dioxide against microbes, spores, and proteins are clear, the mechanisms of action remain poorly defined or unknown.

Since microbes are metabolically active, they have ways to combat or defend against the damaging effects of carbon dioxide (e.g., permeability barriers and active transport processes). These microbe defenses must be overwhelmed before killing effects of carbon dioxide are observed. For this reason, the use of carbon dioxide against microbes is generally accomplished at high pressures of about 30 MPa where the carbon dioxide can rapidly cross the cell membrane and accumulate to high intracellular levels.

Use of high pressure carbon dioxide also has been shown to be effective for inactivating spores that are metabolically inert. High pressure carbon dioxide has also been used to inactivate proteins at temperatures where thermal inactivation is ineffective.

However, use of high pressure carbon dioxide that is at or near its supercritical state may not be suitable for virus inactivation during biopharmaceutical manufacturing or the manufacturing and processing of other sensitive products as the high pressure carbon dioxide may damage the biopharmaceutical or other sensitive products. Furthermore, expensive equipment is required to handle carbon dioxide that is at or near its supercritical state, which often renders such treatment processes economically infeasible.

As shown in FIG. 1, a common virus control strategy may typically involve both lowering the pH of the product solution followed by one or more purification and filtration steps to inactivate or remove active virus contaminants. As the variety of potential virus contaminants is great, the use of multiple virus removal or inactivation techniques with different modes of action is highly desirable to ensure unexpected or untested virus threats will be mitigated. In some cases, manufacturers are hindered in optimizing their downstream operations to eliminate un-necessary purification steps, because those steps contribute to their overall virus safety assurance. The selection of virus inactivation techniques for a given biopharmaceutical manufacturing process generally reflects a compromise between the desire to achieve high product yield at reasonable cost versus the need to reduce the risk of virus contamination to acceptably low levels and provide a safe product.

What is needed therefore is an economical method of virus inactivation before, during and/or after biopharmaceutical or other sensitive product manufacturing that is effective for inactivating viruses, provides an orthogonal mode of action to enhance the overall robustness of the virus inactivation strategy, and minimizes any damage or destruction of the biopharmaceutical or sensitive products.

SUMMARY OF THE INVENTION

The present disclosure may be broadly characterized as a method for virus inactivation in the production, processing, storage or shipping of biological or other sensitive substance comprising the steps of dissolving carbon dioxide into a composition containing the biological or other sensitive substance, or otherwise exposing the biological or other sensitive substance to carbon dioxide; and treating the composition containing the biological or other sensitive substances with said dissolved carbon dioxide at a temperature and pressure substantially less than critical temperature and pressure for a prescribed treatment time to inactivate viruses contained within the composition containing the biological or other sensitive substances. In some embodiments, the biological or other sensitive substance may be frozen and therefore the carbon dioxide is otherwise exposed to the substance as opposed being dissolved into the substance.

The method for virus inactivation may optionally include the additional step of concurrently or sequentially subjecting the composition containing the biological or other sensitive substances with an acid treatment to lower the pH of the composition and inactivate viruses contained within the composition containing the biological or other sensitive substances. Preferably, the carbon dioxide treatment involves sparging carbon dioxide gas into the composition until the composition is saturated with carbon dioxide and is conducted at pressures below 5 MPa; at a temperature of less than or equal to 30° C.; and for a treatment time of between about one minute to about 2000 minutes (although the method could include the storage and/or shipping of substances in the carbon dioxide saturated state for an undetermined time frame that exceeds about 30 minutes). The method for virus inactivation may optionally include the step of stripping the carbon dioxide from the composition with nitrogen or other inert stripping gas after the carbon dioxide treatment.

The present disclosure may also be described as a viral inactivation where powder media, biologic or other sensitive substances are reconstituted with a fluid or diluent that has been previously substantially saturated with carbon dioxide and is then held at a pressure below about 5 MPa; at a temperature of less than or equal to about 30° C.; and for a time of between about one minute to about 2000 minutes, or at other suitable conditions as described herein.

The present disclosure may also be characterized as a system for virus inactivation during the production and/or processing of biological or other sensitive substances comprising: (i) a vessel adapted to hold a composition of biological or other sensitive substances; (ii) a carbon dioxide supply circuit or other carbon dioxide source connected to the vessel for supplying carbon dioxide at a pressure substantially less than critical pressure and temperature to the vessel and substantially dissolving the carbon dioxide into the composition containing the biological or other sensitive substances; and (iii) a control unit operatively associated with the vessel and carbon dioxide supply circuit to substantially saturate the composition within the vessel with carbon dioxide for a prescribed treatment time so as to inactivate viruses contained within the biological or other sensitive substances and associated media, all of which may or may not be designed for single-use applications and (iv) an optional control system to control the pressure and temperature of the vessel for the optimal balance of carbon dioxide saturation and impact on the biological or other sensitive substance.

The present disclosure may also be characterized as a method for virus inactivation during the storage or shipment of biological or other sensitive substance comprising the steps of dissolving carbon dioxide into a composition containing the biological or other sensitive substance, or otherwise exposing the composition containing the biological or other sensitive substance to carbon dioxide; and storing or shipping the composition with said dissolved or exposed carbon dioxide in a container that maintains the level of dissolved or exposed carbon dioxide substantially less than critical pressure and temperature for a time sufficient to inactivate viruses contained within the biological or other sensitive substance.

The present disclosure may also be characterized as a system for virus inactivation during the storage and shipping of biological or sensitive substances comprising: (i) a vessel adapted to hold a composition containing biological or other sensitive substances; (ii) a carbon dioxide supply circuit or other supply source connected or connectable to the vessel for supplying carbon dioxide at substantially less than critical pressure and temperature to the vessel and substantially dissolving the carbon dioxide in the composition containing the biological or other sensitive substances; (iii) a control unit operatively associated with the vessel and carbon dioxide supply circuit to substantially saturate the composition within the vessel with carbon dioxide; (iv) an optional control system to control the pressure and temperature of the vessel for the optimal balance of carbon dioxide saturation and impact on the biological or other sensitive substances and (iv) a storage or shipping vessel designed to store the substance at greater than a prescribed or predetermined carbon dioxide saturation for a prescribed minimum or predetermined treatment time; such storage or shipping vessel may or may not be the same as the vessel within which the substance is saturated with the carbon dioxide, so as to inactivate viruses contained within the composition containing the biological or other sensitive substances, or associated media, all of which may or may not be designed for single-use applications.

The present disclosure may also be characterized as a system for virus inactivation during manufacturing, such as viral filtration, or during storage or shipping comprising: (i) a vessel, transfer line, or filter adapted to transfer or process a composition containing the biological or other sensitive substances; (ii) a carbon dioxide supply, a carbon dioxide substantially saturated diluent supply source, or other carbon dioxide supply source connected, connectable to or residing within the vessel, transfer line, filter or media for supplying carbon dioxide at substantially less than critical temperature and pressure to the composition containing the biological or other sensitive substances, all of which may or may not be designed for single-use applications.

Finally, the present disclosure may also be characterized as a method of purification of biological substance or other sensitive substance comprising the steps of: (i) filtering the substance to remove unwanted solid particles from the substance via one or more filtration techniques; (ii) separating unwanted chemical and biological impurities from the substance via one or more chromatography techniques, wherein the one or more chromatography techniques are performed before and/or after the one or more filtration techniques; and (iii) dissolving carbon dioxide into a composition containing the substance and treating the composition with said dissolved carbon dioxide at conditions substantially less than critical pressure and temperature for a prescribed treatment time to inactivate viruses contained within the composition containing the substances, wherein the carbon dioxide treatment occurs before or after the one or more filtration steps and wherein the carbon dioxide treatment occurs before or after the one or more chromatography techniques.

BRIEF DESCRIPTION OF THE DRAWINGS

The above and other aspects, features, and advantages of the present disclosure will be more apparent from the following, more detailed description thereof, presented in conjunction with the following drawings.

FIG. 5 depicts a table showing the virus plaque counts at a variety of serial dilutions for MS2 and T7 phage viruses treated with $CO_2$ while frozen, treated with liquid nitrogen as a control and untreated as a second control.

FIG. 6 depicts a table showing the virus plaque counts at a variety of serial dilutions for MS2 and T7 phage viruses treated with $CO_2$ at 90 psi, treated with liquid nitrogen as a control and untreated as a second control.

DETAILED DESCRIPTION

As disclosed herein, it has been discovered that carbon dioxide at pressures and temperatures substantially less than critical pressure and temperature is useful for virus inactivation in biopharmaceutical or other sensitive substances during manufacturing, storage and shipping where the goal is to inactivate virus without damage to the protein or other sensitive product it contaminates. Sensitive substances are substances that can change or degrade when exposed to viral inactivation processes and include, without limitation, chemicals, vitamins and nutrients.

Surprisingly, the use of carbon dioxide in virus inactivation may not require critical high pressures or super-critical carbon dioxide, unlike the use of carbon dioxide in most bacterial eradication approaches. The effects of dissolved carbon dioxide for virus inactivation also appear to be additive or perhaps even synergistic with other virus inactivating technologies and conditions.

Viral Inactivation Methods

Figure 1:
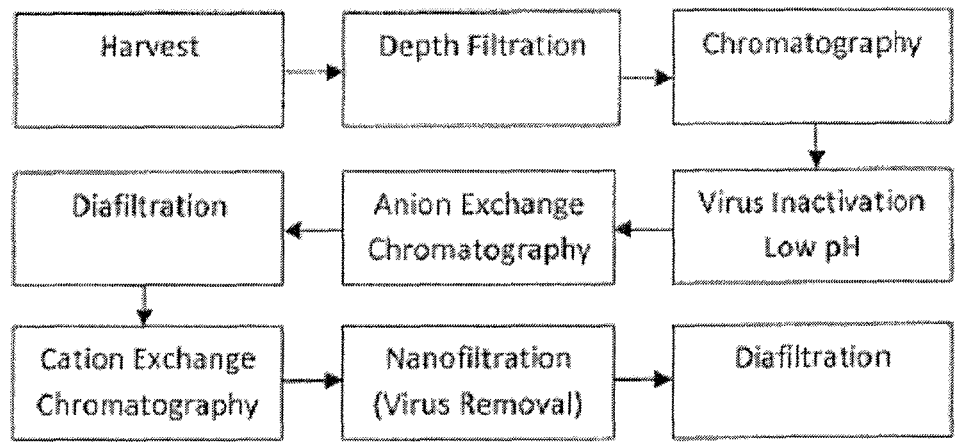
FIG. 1 is a representation of an existing virus inactivation process used in a typical biopharmaceutical manufacturing process.

Turning now to the figures, and more particularly FIG. 1, there is shown a schematic representation of a typical prior art purification process used in the production of biopharmaceutical products. As seen therein, the typical prior art purification process involves several chromatography steps, including cation exchange and anion exchanges, as well as several filtration steps and a low pH virus inactivation step.

Figure 2:
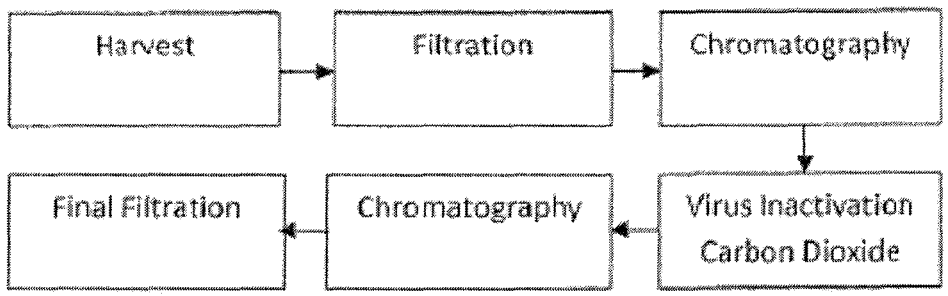
FIG. 2 depicts a carbon dioxide-based virus inactivation process in accordance with an embodiment of the present disclosure.

In contrast, as seen in FIG. 2, an embodiment of the presently disclosed method of purification of biological substances involves one or more filtration steps, one or more chromatography steps, and virus inactivation step comprising low to moderate and substantially less than critical pressure and temperature carbon dioxide treatment. The preferred carbon dioxide treatment involves dissolving carbon dioxide gas substantially less than critical pressure and temperature into a composition containing a substance via a sparger or other carbon dioxide saturation apparatus until the composition is saturated with carbon dioxide. The carbon dioxide saturated composition is held for a prescribed treatment time sufficient to inactivate viruses contained within the composition. The carbon dioxide treatment may be performed before and/or after the filtration steps and chromatography steps. After the carbon dioxide treatment, the carbon dioxide is optionally stripped from the composition with nitrogen or other inert stripping gas after the carbon dioxide treatment.

In one embodiment, the step of dissolving carbon dioxide into the substance further comprises the exposure of the substance to dry ice. The dry ice may be contained in a compartment for the storage of solid carbon dioxide that may be coupled in connection with a vessel for supplying carbon dioxide to a biological or other sensitive substance. The compartment may or may not be the same as the vessel for holding the biological or other sensitive substance.

As used herein, the phrase "composition containing biological or other sensitive substances," and similar phrases refers to both the substance or substances themselves and any solution or solid containing the substance or substances. For example, the substance could be a solution, frozen solution, or powder containing a protein, cell, nutrient or vitamin. Alternatively, it could be a protein, cell, nutrient or vitamin (e.g., purified and isolated proteins, cell, nutrients or vitamins).

In the preferred purification methods, the one or more filtration steps may involve commonly used filtration techniques such as reverse osmosis, ultrafiltration, nanofiltration, microfiltration, and diafiltration, etc. to remove unwanted solid particles from the composition. Likewise, the preferred chromatography steps involve commonly used chromatography techniques, for example, ion exchange chromatography to separate unwanted chemical and biological impurities from the composition containing the substances.

Figure 3A:
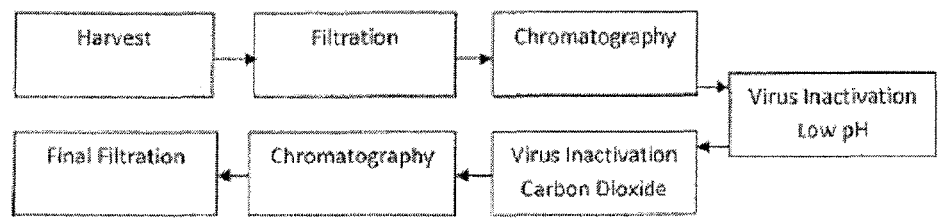
FIGS. 3A and 3B depict a carbon dioxide based virus inactivation process in accordance with other embodiments of the present disclosure.
Figure 3B:
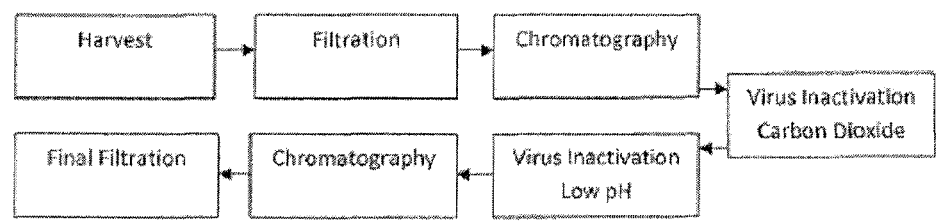
Figure 4:
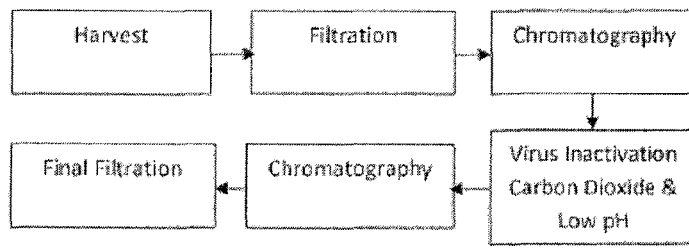
FIG. 4 depicts yet another embodiment of the carbon dioxide based virus inactivation process in accordance with the present disclosure.

Alternate embodiments of the present purification methods for biological substances and associated virus inactivation methods are shown in FIGS. 3A, 3B, and 4. FIGS. 3A and 3B depict a purification method similar to that shown in FIG. 2 but with dual virus inactivation steps, namely an acid or low pH treatment and the carbon dioxide treatment, performed in succession or sequentially FIG. 4 depicts another purification method with dual virus inactivation steps performed concurrently. In this embodiment, the composition containing the biological or other sensitive substances is subjected to the low pH or acid treatment and the carbon dioxide treatment in the same step. For example, carbon dioxide can be dissolved into the composition during an acid-based virus inactivation step to achieve greater virus kill or inactivation at similar pH levels or achieve equivalent virus kill at more neutral or tolerant pH levels for the product. Most viral inactivation for biologics is performed at a pH between about 3 and 4. The pH level of the composition is preferably optimized by controlling the amount of acid added to the composition and/or the optional use of a pH buffering solution. The present disclosure may further comprise the step of adding a buffer during the carbon dioxide treatment to maintain the pH level of the composition between about 4.0 and about 9.0, preferably between about 4.5 and about 8.5 and more preferably about 5.5 and about 8.0, or any combination of these values. As the pH of the composition approaches 7, pH sensitive samples are less likely to be affected. Effective viral inactivation may also be obtained wherein the pH level of the composition is held at a pH greater than about 3.0, or about 3.5, or about 4.0, or about 4.5, or about 5.0, or about 5.5, or about 6.0, or about 6.5 or about 6.8, or about 7.0.

As suggested in FIGS. 3A, 3B, and 4, the efficacy of carbon dioxide treatment for virus inactivation may be enhanced by combining the present carbon dioxide treatment method with other methods known to promote virus inactivation. For example, carbon dioxide treatment could be combined with treatment by temperature control, solvent, detergent, alcohol or other chemicals. It should be noted that the chemical equilibria of dissolved carbon dioxide, bicarbonate, and carbonate species is pH dependent, and it is anticipated that the efficacy of carbon dioxide treatment can be adjusted by modifying the pH of the solution and that one or more optimal pHs may exist for achieving greatest inactivation of a given virus species without compromising the quality of the desired biopharmaceutical product. It also should be noted that carbon dioxide saturation can be increased by adjusting pressure and temperature (e.g. increasing pressure and/or decreasing temperature) and that the process can be further optimized by controlling these parameters to create an optimal balance of saturation, impact on the sensitive product, and cost. The combination of carbon dioxide treatment with other virus inactivation treatments can occur in the same treatment vessel or in closely sequenced steps where the virus species are still sensitized to the treatment of the first virus inactivation step when they enter the second virus inactivation step.

Preferably, the carbon dioxide treatment introduces (e.g., sparges) carbon dioxide gas into the composition until the composition is saturated with carbon dioxide to the point where inactivation occurs, although alternate dissolution techniques may be used. The carbon dioxide treatments are preferably conducted at pressures below about 5 MPa and temperatures below about 30° C., which is substantially below the critical pressure temperature and pressure which is nominally about 7.38 MPa and 31° C. The pressure and temperature can be controlled to maximize the carbon dioxide saturation to provide at least a 80% reduction in the target virus or viruses, while minimizing the impact on the sensitive substance. Unlike the carbon dioxide sterilization techniques, the temperature of the solution containing the biological substance during the carbon dioxide virus inactivation treatments is preferably less than or equal to about 30° C., with lower temperatures generally improving the dissolution of the carbon dioxide in solution. Viral inactivation through carbon dioxide saturation does not have to occur while the substance is in the liquid phase, and may preferentially occur while in the solid phase or during phase transitions.

The carbon dioxide treatments may also be conducted at pressures below about 4.5 MPa, about 4.0 MPa, about 3.5 MPa, about 3.0 MPa, about 2.5 MPa, about 2.0 MPa, about 1.5 MPa, or about 1.0 MPa. The carbon dioxide treatments may also be conducted at temperatures below about 30° C., about 28° C., about 26° C., about 25° C., about 24° C., about 22° C., and about 20° C. Preferably, the compositions and methods of the present disclosure are capable of at least a 90% reduction in the target virus or viruses, at least a 99% reduction in the target virus or viruses, at least a 99.9% reduction in the target virus or viruses, at least a 99.99% reduction in the target virus or viruses, or at least a 99.999% reduction in the target virus or viruses depending on the conditions used and the virus or viruses targeted.

The preferred carbon dioxide treatment times range between about one minute to about 2000 minutes, and more preferably between about one minute and about 24 hours. In cases where the product is stored or shipped in the carbon dioxide saturated state, these times may be longer.

It should be recognized that the carbon dioxide treatment scheme described above can, in principle, be implemented at any point in the biopharmaceutical or other sensitive substance production route following product synthesis and on any of the raw materials entering the production process. A practical implementation scheme would be to add carbon dioxide to a composition containing a biopharmaceutical substance during the low pH virus inactivation step. The carbon dioxide could be introduced into the composition before entering the vessel where the low pH step is performed, or the carbon dioxide could be introduced into the composition within the low pH inactivation vessel. For a given pH, the addition of carbon dioxide would increase the level of virus inactivation. For a desired level of virus inactivation, the addition of carbon dioxide would enable the use of higher pH and thereby reduce the potentially damaging effects of more acidic environments on the biopharmaceutical product. For example, viral inactivation of blood products is often performed at pH 4, and the addition of carbon dioxide treatment could allow for either equivalent inactivation at higher pH or higher inactivation at pH 4. As mentioned above, the degree of inactivation in a process combining low pH and carbon dioxide treatment can be enhanced by lowering the temperature, or increasing the carbon dioxide pressure or by increasing the carbon dioxide treatment time.

A number of different systems or schemes are envisioned for exploiting the ability of carbon dioxide to inactive viruses in biological or other sensitive substances. In one embodiment, the biological substances is held in a disposable or non-disposable vessel. Carbon dioxide is introduced into a composition containing the substance either before entering the vessel or within the vessel. As described herein, the dissolved carbon dioxide inactivates or kills the viruses within the composition. The degree of inactivation can be enhanced by decreasing the temperature, increasing the carbon dioxide pressure, or increasing the carbon dioxide treatment time.

Additionally, the introduction of the carbon dioxide into the sensitive substance can either be done directly, or through the introduction of liquids already saturated with carbon dioxide. This is demonstrated by the case where dry powders or concentrated forms, like cell culture media, are reconstituted with sterile water that is pre-saturated with carbon dioxide.

Viral Inactivation can occur during the manufacturing process, but also before the process, as in the case of raw materials like cell culture or fermentation media, or after the process. For example, viral inactivation can occur for biological or other sensitive substances during the storage or shipping process through the saturation with carbon dioxide and the storage or shipping in a vessel that maintains the carbon dioxide levels for a prescribed minimum or predetermined period of time.

It should be also noted that the vessels mentioned above and their associated components (e.g., impellers for mixing, gas injection nozzles, spargers, etc.) can be fabricated from metallic or polymeric materials. Metallic vessels will generally be constructed of stainless steel and designed for clean-in-place and steam-in-place operation following well established industry standards. A fully polymeric carbon dioxide treatment vessel lends itself to disposable use where the vessel may be discarded between batches to avoid the time and expense of cleaning operations. In one currently preferred embodiment, existing vessels, bioreactors, etc. could be used with minimal potential retrofit.

EXAMPLES

Experiments were run to demonstrate that carbon dioxide treatment at less than critical temperature and pressure can cause viral inactivation. Also, it was investigated whether different temperatures and pressures can effect the level of inactivation.

Experiment 1

VIRAPUR MS2 bacteriophage and T7 bacteriophage were treated with carbon dioxide at less than critical temperature and pressure. MS2 phage is a small RNA phage. T7 is a large DNA Phage. They represent two different types of bacteriophage. A 1:100 dilution was made of each original stock of phage (original concentration is as provided) into water for irrigation buffered with 10 mM Phosphate, pH 7.2. Three separate 1 ml samples in 10 ml plastic tubes were made of each phage. One tube was placed in a liquid nitrogen dewer. Into the second tube was placed a 2 $cm^3$ piece of dry ice. The third tube was left at room temperature. Treatment lasted until the dry ice treated tube had fully melted, or about 45 minutes. After treatment, phage samples were diluted as delineated in FIG. 5 and plated on agar plates containing their corresponding host bacteria for Plaque forming units (PFU). After plaques had developed, they were counted. Plaque counts are also shown in FIG. 5. The results show a significant decrease in the number of viable phage particles for MS2 and T7 phage after treatment with carbon dioxide at less than critical temperature and pressure (atmospheric).

Experiment 2

A 1:100 dilution was made of each original stock of phage for the two phages in the first experiment into water for irrigation buffered with 10 mM Phosphate, pH 7.2. A device capable of holding 150 psi of pressure was used for the treatment of phage with high pressure $CO_2$ gas. After titration with various amounts of dry ice, it was determined that 0.8 grams of dry ice would hold the pressure of 90 psi for at least one hour without causing the device to release pressure.

Samples of phage in buffered water were either treated with the experimental pressurized $CO_2$, with liquid nitrogen or left at room temperature for the duration of the pressure treatment. Multiple phage samples (MS2 and T7) were treated simultaneously in the pressure device. After one hour of pressure treatment, the pressure in the device was released and the phage samples removed and titered for PFU. They were diluted as described in FIG. 6 and plated on agar plates containing their corresponding host bacteria. After plaques had developed, they were counted. Plaque counts are shown in FIG. 6. The result show a significant decease (about one log) in the number of viable phage particles in the MS2 phage and no significant decrease with T7 phage after treatment with carbon dioxide at less than critical temperature and pressure (90 psi). After treatment with 90 psi $CO_2$ gas for one hour, samples had a pH of about 6.

INDUSTRIAL APPLICABILITY

The benefits of using carbon dioxide at substantially less than critical pressure and temperature in virus inactivation processes during biopharmaceutical, liquid nutrition or other sensitive product manufacturing, shipping or storage is clear and represents an attractive solution for bio-manufacturing and other applications, both from a technical and economic perspective. The disclosed methods and systems are compatible with current bio-manufacturing, raw material, and nutrition manufacturing processes. More advantageously, the presently disclosed methods and systems are unlikely to damage product or cause adverse effects and can be easily implemented and removed, as required. The disclosed methods provide a new approach and mode-of-action for inactivating viruses and thereby provide a means for biopharmaceutical and other manufacturers to enhance their overall virus safety assurance.

Significant virus inactivation can be achieved using the above-described carbon dioxide methods with or without acidic treatments. This, in turn, could yield significant cost savings in the biopharmaceutical manufacturing industry by optimizing downstream purification to eliminate un-necessary steps that are only preserved for their small contributions to the total virus log reductions. These downstream chromatography (e.g., ion exchange chromatography, etc.) and filtration steps (e.g., ultrafiltration, nanofiltration, microfiltration, diafiltration, etc.) are often highly expensive and individually have small incremental increases in virus inactivation. In short, the present system and method of virus inactivation could potentially allow implementation of new purification protocols with fewer steps, leading to substantial cost savings.

Additionally, there have been a number of recent, extremely costly and dangerous facility contaminations due to viral contaminations. These events result in costly plant shut-downs and product recalls. Raw materials including culture media are seen as potential entry-points for these contaminations. The availability of an orthogonal viral inactivation technology that does not impact the efficacy of the raw materials could dramatically reduce facility contaminations and their significant economic impact.

Since many of the current and planned biopharmaceutical and liquid nutrition products/therapies are extremely expensive, changes to the purification process that reduce overall product loss and product damage would appear to be commercially advantageous. Reducing the total number of purification steps could have a significant value to the biopharmaceutical manufacturing industry in the form of greater product yields. Additionally, the present virus inactivation method and system using carbon dioxide, without aggressively low pH acid treatments, can help achieve virus inactivation targets without causing product denaturation.

While the biopharmaceutical and other manufacturing industries employ a variety of different virus inactivation or reduction methods, little-to-no viral inactivation methods are used to reduce or eliminate the contamination of bio-samples targeted for long-term storage. Furthermore, with the growth of personalized cell therapies, methods that reduce or eliminate any potential virus contamination will be employed only if there is no disruption of the therapy itself. The application of the present carbon dioxide virus inactivation process could be advantageous to the biobanking and repository community as rare samples and personalized medicine becomes an ever more important part of the industry. In this regard, the present carbon dioxide virus inactivation system and methods are suitable for use or application in cell therapies and bio-repositories.

Because viruses are resistant to cold temperatures, long term cryogenic storage is unlikely to remove any present contamination in critical samples for biobanks and repositories. Even if the carbon dioxide-based virus inactivation treatment described herein fails to fully destroy the virus, a lowering of the viral load below a critical threshold has the potential to remove concerns about infection. Additionally, carbon dioxide viral inactivation could prove particularly efficacious during storage as carbon dioxide saturation is higher at reduced temperatures. If high inactivity can be achieved, it not only improves sample quality and preservability but also improves safety concerns over handling contaminated samples by laboratory personal and hospital staff and in processing equipment that might be shared but not effectively clean of viral contamination, such as (LN2) storage and controlled rate freezers.

From the foregoing, it should be appreciated that the present disclosure provides effective methods and systems for virus inactivation using carbon dioxide in biopharmaceutical and other sensitive produce manufacturing, processing, shipping and storage. While the invention herein disclosed has been described by means of specific embodiments and processes associated therewith, numerous modifications and variations can be made thereto by those skilled in the art without departing from the scope of the invention as set forth in the claims or sacrificing all of its features and advantages.

What is claimed is:

1. A method for virus inactivation in the production, processing, storage or shipping of a biological or other sensitive substance comprising the steps of:
   dissolving carbon dioxide into a composition containing the biological or other sensitive substance, or otherwise exposing the biological or other sensitive substance to carbon dioxide, wherein the step of dissolving carbon dioxide into the composition further comprises sparginq carbon dioxide gas into the composition until the composition is substantially saturated with carbon dioxide; and
   treating the composition containing the biological or other sensitive substance with said carbon dioxide at a temperature and pressure substantially less than critical pressure and temperature for a prescribed treatment time to inactivate at least 80% of a target virus or viruses contained within the composition containing the biological or other sensitive substance; wherein the composition is maintained at temperatures of less than or equal to 30° C. during the carbon dioxide treatment.

2. The method of claim 1 further comprising the step of treating the composition with an acid to lower the pH of the composition and inactivate viruses contained within the biological or other sensitive substances.

3. The method of claim 1 wherein the carbon dioxide treatment is conducted at pressures below about 5 Mpa.

4. The method of claim 1 wherein the treatment time for the carbon dioxide treatment is between about 1 minute and about 2000 minutes.

5. The method of claim 1 further comprising the step of adding a buffer solution during the carbon dioxide treatment to maintain the pH level of the solution between 5.5 and 8.0.

6. The method of claim 1 wherein the step of dissolving carbon dioxide into the composition further comprises adding dry ice, liquid carbon dioxide, or a solution that is substantially saturated with carbon dioxide to the biological or other sensitive substance that is in a concentrated or powder form.

7. The method of claim 1 wherein the step of dissolving carbon dioxide into the substance further comprises the exposure of the substance to dry ice.

8. The method of claim 1 wherein the biological or other sensitive substance is a cell culture, fermentation media, infant formula, nutrition product, blood, cell therapy, protein, or pharmaceutical product.

9. The method of claim 1 further comprising the step of stripping the carbon dioxide from the composition with nitrogen or other inert stripping gas after the carbon dioxide treatment.

10. A method for virus inactivation during the storage or shipment of biological or other sensitive substance comprising the steps of:
    dissolving carbon dioxide into a composition containing the biological or other sensitive substance, or otherwise exposing the composition containing the biological or other sensitive substance to carbon dioxide; wherein the step of dissolving carbon dioxide into the composition further comprises sparging carbon dioxide gas into the composition until the composition is substantially saturated with carbon dioxide; and
    storing or shipping the composition with said dissolved or exposed carbon dioxide in a container that maintains the level of dissolved or exposed carbon dioxide at a pressure and temperatures but substantially less than critical pressure and temperature for a time sufficient to inactivate at least 80% of a target virus or viruses contained within the biological or other sensitive substance; wherein the composition is maintained at temperatures of less than or equal to about 30° C. during the time sufficient for inactivation.

11. The method of claim 10 further comprising the step of treating the composition with an acid to lower the pH of the composition and inactivate viruses contained within the biological or other sensitive substance.

12. The method of claim 10 wherein the carbon dioxide treatment is conducted at a pressure below about 5 MPa.

13. The method of claim 10 wherein the treatment time for the carbon dioxide treatment is at least about 30 minutes.

14. The method of claim 10 further comprising the step of adding a buffer during the carbon dioxide treatment to maintain the pH level of the composition between about 5.5 and about 8.

15. The method of claim 10 wherein the step of dissolving carbon dioxide into the composition further comprises adding dry ice, liquid carbon dioxide, or a solution that is substantially saturated with carbon dioxide to the biological or other sensitive substance that is in a concentrated or powder form.

16. The method of claim 10 further comprising the step of substantially stripping the carbon dioxide from the composition with nitrogen or another inert gas after the shipping or storage.

17. The method of claim 10 further comprising the saturation of carbon dioxide through the storage or shipping on dry ice.

* * * * *